US007132246B2

(12) United States Patent
Bergmann et al.

(10) Patent No.: US 7,132,246 B2
(45) Date of Patent: Nov. 7, 2006

(54) USE OF SOLUBLE CYTOKERATIN-1-FRAGMENTS IN DIAGNOSTICS AND THERAPY

(76) Inventors: Andreas Bergmann, Baum läuferweg 47, 12351 Berlin (DE); Joachim Struck, Holsteinische Str. 28, 12161 Berlin (DE); Monika Ühlein, Humfelandstrase 15, 10407 Berlin (DE)

( * ) Notice: Subject to any disclaimer, the term of this patent is extended or adjusted under 35 U.S.C. 154(b) by 0 days.

(21) Appl. No.: 10/480,848

(22) PCT Filed: Jun. 12, 2002

(86) PCT No.: PCT/EP02/06473

§ 371 (c)(1),
(2), (4) Date: Jun. 1, 2004

(87) PCT Pub. No.: WO03/002600

PCT Pub. Date: Jan. 9, 2003

(65) Prior Publication Data

US 2004/0219597 A1 Nov. 4, 2004

(30) Foreign Application Priority Data

Jun. 27, 2001 (DE) ................................ 101 30 985

(51) Int. Cl.
*G01N 33/53* (2006.01)

(52) U.S. Cl. .......................... 435/7.1; 514/12; 530/300

(58) Field of Classification Search .................. 514/12
See application file for complete search history.

(56) References Cited

U.S. PATENT DOCUMENTS

| | | | |
|---|---|---|---|
| 5,527,773 A | 6/1996 | Steinert et al. | 514/12 |
| 5,639,617 A | 6/1997 | Bohuon | 435/7.1 |
| 5,660,994 A * | 8/1997 | Bruder-Heid et al. | 435/7.23 |
| 6,190,872 B1 * | 2/2001 | Slotman | 435/7.92 |

FOREIGN PATENT DOCUMENTS

| | | |
|---|---|---|
| DE | 198 47 690 A1 | 4/2000 |
| EP | 0 163 304 A2 | 12/1985 |
| EP | 0 267 356 B1 | 1/1991 |
| EP | 0 267 355 B1 | 9/1991 |
| EP | 0 337 057 B1 | 4/1993 |
| EP | 0 656 121 B1 | 3/1998 |
| WO | WO 97 25622 A | 7/1997 |
| WO | WO 00/22439 | 4/2000 |
| WO | WO 01/12212 A | 2/2001 |

OTHER PUBLICATIONS

Hotchkiss, R. and Karl,I. N Eng J Med 348:2 138-150 (2003).*
Aird, W. Mayo Clin Proc. 78: 869-881 (2003).*
Carrigan, S. et al. Clinical Chemistry 50:8 1301-1314 (2004).*
NCBI FASTA protein sequence of keratin I Dec. 10, 1999.*
NCBI FASTA protein sequence of interleukin-6 Aug. 6, 2006.*

Assicot, et al., "High Serum Procalcitonin Concentrations in Patients with Sepsis and Infection," *Lancet*, 341(8844):515-518, 1993.

Beishuizen et al., "Endogenous Mediators in Sepsis and Septic Shock," *Advances Clin. Chem.*, 363:55-131, 1999.

Calandra et al., "Protection from Septic Shock by Neutralization of Macrophage Migration Inhibitory Factor," *Nature Medicine*, 6(2):164-170, 2000.

Gabay and Kushner, "Acute-Phase Proteins and Other Systemic Responses to Inflammation," *New Engl. J. Med.*, 340(6):448-454, 1999.

Garber, "Protein C May Be Sepsis Solution," *Nature Biotechnology*, 18:917-918, 2000.

Ghillani et al., "Monoclonal Antipeptide as Tools to Dissect Closely Related Gene Products," *J. Immunol.*, 141(9):3156-3163, 1988.

Ghillani et al., "Identification and Measurement of Calcitonin Precursors in Serum of Patients with Malignant Diseases," *Cancer Research*, 49(23):6845-6851, 1989.

Heukeshoven and Dernick, "Improved Silver Staining Procedure for Fast Staining in PhastSystem Development Unit. I. Staining of Sodium Dodecyl Sulfate Gels," *Electrophoresis*, 9(1):28-32, 1988.

Joseph et al., "Factor XII-Dependent Contact Activation on Endothelial cells and Binding Proteins gClqR and Cytokeratin 1," *Throm. Haemost.*, 85:119-124, 2001.

Joseph et al., "Activation of the Kinin-Forming Cascade on the Surface of Endothelial Cells," *Biol. Chem.*, 382:71-75, 2001.

Kanazawa et al., "CYFRA 21-1, A Cytokeratin Subunit 19 Fragment, in Bronchoalveolar Lavage Fluid from Patients with Interstitial Lung Disease," *Clin. Sci.*, 94:531-535, 1998.

Kaplan et al., "Activation of the Plasma Kinin Forming Cascade Along Cell Surfaces," *Int. Arch. Allergy Immunol.*, 124:339-341, 2001.

Karzai, et al., "Procalcitonin—A New Indicator of the Systemic Response to Severe Infections," *Infections*, 25:3-8, 1997.

Klose, "Fractionated Extraction of Total Tissue Proteins from Mouse and Human for 2-D Electrophoresis," *In: Methods in Molecular Biology, vol. 112, 2-D Proteame Analysis Protocols*, Humana Press Inc., N.J., pp. 67-85.

Klose and Kobalz, "Two-Dimensional Electrophoresis of Proteins: An Updated Protocol and Implications for a Functional Analysis of the Genome," *Electrophoresis*, 16:1034-1059, 1995.

Lamerdin et al., EMBL Database Accession No. 075272.

Lingner et al., "Reverse Transcriptase Motifs in the Catalytic Subunit of Telomerase," *Science*, 276:561-567, 1997.

Lucas et al., "Aberrantly Expressed Cytokeratin 1, A Tumor-Associated Autoantigen in Papillary Thyroid Carcinoma," *Int. J. Cancer*, 73:171-177, 1997.

(Continued)

*Primary Examiner*—Robert A. Wax
*Assistant Examiner*—Anand Desai
(74) *Attorney, Agent, or Firm*—Heslin Rothenberg Farley & Mesiti P.C.; Kathy Smith Dias

(57) ABSTRACT

Use of novel soluble cytokeratin 1 fragments from body fluids or body tissues as marker peptides for the diagnosis, prognosis and monitoring of the course of inflammations and infections and/or as a target for the therapeutic influencing of the course of inflammations and/or infections.

7 Claims, 5 Drawing Sheets

OTHER PUBLICATIONS

Figures 1A, 1B:
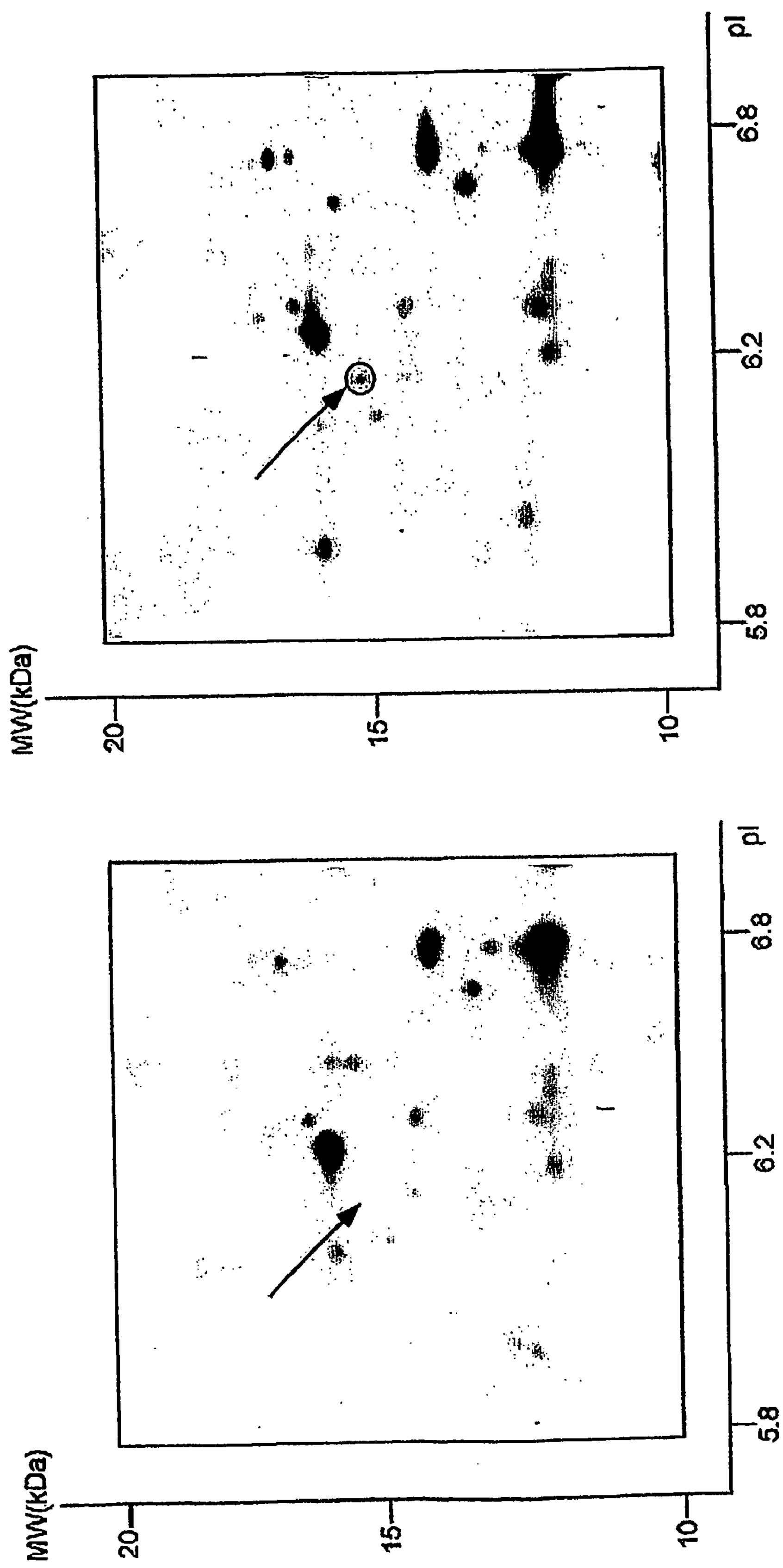

Lucas et al., "Identification of a 35 kD Tumor-Associated Autoantigen in Papillary Thyroid Carcinoma," *Anticancer Research*, 16:2493-2496, 1996.
Mann and Pandey, "Use of Mass Spectrometry-Derived Data to Annotate Nucleotide and Protein Sequence Databases," *TRENDS Biochem. Sci.*, 26(1):54-61, 2001.
Neubauer et al., Mass Spectrometry and EST-Database Searching Allows Characterization of the Multi-Protein Spliceosome Complex, *Nature Genetics*, 20:46-50, 1998.
Neuhoff et al., "Improved Staining of Proteins in Polyacrylamide Gels Including Isoelectric Focusing Gels with Clear Background at Nanogram Sensitivity Using Coomassie Brilliant Blue G-250 and R-250," *Electrophoresis*, 9:255-262, 1988.
Oczenski et al., "Procalcitonin: A New Parameter for the Diagnosis of Bacterial Infection in the Peri-Operative Period," *Eur. J. Anaesthesiol.*, 15:202-209, 1998.
Omary et al., "Keratin Modifications and Solubility Properties in Epithelial Cells and *In vitro,*" *Subcellular Biochemistry*, 31:105-140, 1998.
Otto et al., "Identification of Human Myocardial Proteins Separated by Two-Dimensional Electrophoresis Using an Effective Sample Preparation for Mass Spectrometry," *Electrophoresis*, 17:1643-1650, 1996.
Panacek, "Anti-TNF Strategies," *Intensive Care Med.*, 23:1144-1149, 1997.
Presland, "Epithelial Structural Proteins of the Skin and Oral Cavity: Function in Health and Disease," *Crit. Rev. Oral. Biol. Med.*, 11(4):383-408, 2000.
Redl et al., "Procalcitonin Release Patterns in a Baboon Model of Trauma and Sepsis: Relationship to Cytokines and Neopterin," *Crit. Care Med.*, 28(11):3659-3663, 2000.
Redl and Schlag, "Non-Human Primate Models of Sepsis," *Sepsis*, 2:243-253, 1998.
Reinhart et al., "Sepsis Und Spetischer Schcok," *Intensivmedizin*, 756-760, 2001.
Shariat-Madar and Schmaier, "Kininogen-Cytokeratin 1 Interactions in Endothelial Cell Biology," *Trends Cardiovasc. Med.*, 9(8):238-244, 1999.
Shariat-Madar et al., "Mapping Binding Domains of Kininogens on Endothelial Cell Cytokeratin 1," *J. Biol. Chem.*, 274(11):7137-7145, 1999.
Stieber, "34.10 CYFRA 21-1 (Cytokeratin-19-Fragmente)," *Thomas Labor Diagnose*, 987-992.
Stigbrand, "The Versatility of Cytokeratins as Tumor Markers," *Tumor Biol.*, 22:1-3, 2001.
Wiedenmann et al., "Cytokeratin Fragments in Serum Possible New Markers for the Follow-up of Patients with Inflammatory Liver Disease," *Gastroenterology*, 96(5);A673, 1989.
International Search Report for PCT/EP 02/06473, mailed Nov. 6, 2002.

* cited by examiner

SEQUENCE LISTING

```
<160> NUMBER OF SEQ ID NOS: 5

<210> SEQ ID NO 1
<211> LENGTH: 12
<212> TYPE: PRT
<213> ORGANISM: Primat (Pavian)

<400> SEQUENCE: 1

Ser Leu Asn Asn Gln Phe Ala Ser Phe Ile Asp Lys
  1               5                  10


<210> SEQ ID NO 2
<211> LENGTH: 11
<212> TYPE: PRT
<213> ORGANISM: Primat (Pavian)

<400> SEQUENCE: 2

Thr Asn Ala Glu Asn Glu Phe Val Thr Ile Lys
  1               5                  10


<210> SEQ ID NO 3
<211> LENGTH: 643
<212> TYPE: PRT
<213> ORGANISM: Homo sapiens
<300> PUBLICATION INFORMATION:
<302> TITLE: L.Johnson et al., Structure of a gene for the human
      epidermal 67-kDa keratin
<303> JOURNAL: Proc. Natl. Acad. Sci. U.S.A.
<304> VOLUME: 1985
<305> ISSUE: 82
<306> PAGES: 1896-1900

<400> SEQUENCE: 3

Ser Arg Gln Phe Ser Ser Arg Ser Gly Tyr Arg Ser Gly Gly Gly Phe
  1               5                  10                  15

Ser Ser Gly Ser Ala Gly Ile Ile Asn Tyr Gln Arg Arg Thr Thr Ser
             20                  25                  30

Ser Ser Thr Arg Arg Ser Gly Gly Gly Gly Gly Arg Phe Ser Ser Cys
         35                  40                  45

Gly Gly Gly Gly Gly Ser Phe Gly Ala Gly Gly Gly Phe Gly Ser Arg
     50                  55                  60

Ser Leu Val Asn Leu Gly Gly Ser Lys Ser Ile Ser Ile Ser Val Ala
 65                  70                  75                  80

Arg Gly Gly Gly Arg Gly Ser Gly Phe Gly Gly Gly Tyr Gly Gly Gly
                 85                  90                  95
```

-continued

```
Gly Phe Gly Gly Gly Gly Phe Gly Gly Gly Gly Phe Gly Gly Gly Gly
            100                 105                 110

Ile Gly Gly Gly Gly Phe Gly Gly Phe Gly Ser Gly Gly Gly Gly Phe
        115                 120                 125

Gly Gly Gly Gly Phe Gly Gly Gly Gly Tyr Gly Gly Gly Tyr Gly Pro
    130                 135                 140

Val Cys Pro Pro Gly Gly Ile Gln Glu Val Thr Ile Asn Gln Ser Leu
145                 150                 155                 160

Leu Gln Pro Leu Asn Val Glu Ile Asp Pro Glu Ile Gln Lys Val Lys
                165                 170                 175

Ser Arg Glu Arg Glu Gln Ile Lys Ser Leu Asn Asn Gln Phe Ala Ser
            180                 185                 190

Phe Ile Asp Lys Val Arg Phe Leu Glu Gln Gln Asn Gln Val Leu Gln
        195                 200                 205

Thr Lys Trp Glu Leu Leu Gln Gln Val Asp Thr Ser Thr Arg Thr His
    210                 215                 220

Asn Leu Glu Pro Tyr Phe Glu Ser Phe Ile Asn Asn Leu Arg Arg Arg
225                 230                 235                 240

Val Asp Gln Leu Lys Ser Asp Gln Ser Arg Leu Asp Ser Glu Leu Lys
                245                 250                 255

Asn Met Gln Asp Met Val Glu Asp Tyr Arg Asn Lys Tyr Glu Asp Glu
            260                 265                 270

Ile Asn Lys Arg Thr Asn Ala Glu Asn Glu Phe Val Thr Ile Lys Lys
        275                 280                 285

Asp Val Asp Gly Ala Tyr Met Thr Lys Val Asp Leu Gln Ala Lys Leu
    290                 295                 300

Asp Asn Leu Gln Gln Glu Ile Asp Phe Leu Thr Ala Leu Tyr Gln Ala
305                 310                 315                 320

Glu Leu Ser Gln Met Gln Thr Gln Ile Ser Glu Thr Asn Val Ile Leu
                325                 330                 335

Ser Met Asp Asn Asn Arg Ser Leu Asp Leu Asp Ser Ile Ile Ala Glu
            340                 345                 350

Val Lys Ala Gln Asn Glu Asp Ile Ala Gln Lys Ser Lys Ala Trp Ala
        355                 360                 365

Glu Ser Leu Tyr Gln Ser Lys Tyr Glu Glu Leu Gln Ile Thr Ala Gly
    370                 375                 380

Arg His Gly Asp Ser Val Arg Asn Ser Lys Ile Glu Ile Ser Glu Leu
385                 390                 395                 400

Asn Arg Val Ile Gln Arg Leu Arg Ser Glu Ile Asp Asn Val Lys Lys
                405                 410                 415

Gln Ile Ser Asn Leu Gln Gln Ser Ile Ser Asp Ala Glu Gln Arg Gly
            420                 425                 430

Glu Asn Ala Leu Lys Asp Ala Lys Asn Lys Leu Asn Asp Leu Glu Asp
        435                 440                 445

Ala Leu Gln Gln Ala Lys Glu Asp Leu Ala Arg Leu Leu Arg Asp Tyr
    450                 455                 460

Gln Glu Leu Met Asn Thr Lys Leu Ala Leu Asp Leu Glu Ile Ala Thr
465                 470                 475                 480

Tyr Arg Thr Leu Leu Glu Gly Glu Glu Ser Arg Met Ser Gly Glu Cys
                485                 490                 495

Ala Pro Asn Val Ser Val Ser Val Ser Thr Ser His Thr Thr Ile Ser
            500                 505                 510
```

-continued

```
Gly Gly Gly Ser Arg Gly Gly Gly Gly Gly Gly Tyr Gly Ser Gly Gly
        515                 520                 525

Ser Ser Tyr Gly Ser Gly Gly Gly Ser Tyr Gly Ser Gly Gly Gly Gly
    530                 535                 540

Gly Gly Gly Arg Gly Ser Tyr Gly Ser Gly Gly Ser Ser Tyr Gly Ser
545                 550                 555                 560

Gly Gly Gly Ser Tyr Gly Ser Gly Gly Gly Gly Gly Gly His Gly Ser
                565                 570                 575

Tyr Gly Ser Gly Ser Ser Ser Gly Gly Tyr Arg Gly Gly Ser Gly Gly
            580                 585                 590

Gly Gly Gly Gly Ser Ser Gly Gly Arg Gly Ser Gly Gly Gly Ser Ser
        595                 600                 605

Gly Gly Ser Ile Gly Gly Arg Gly Ser Ser Ser Gly Gly Val Lys Ser
    610                 615                 620

Ser Gly Gly Ser Ser Ser Val Arg Phe Val Ser Thr Thr Tyr Ser Gly
625                 630                 635                 640

Val Thr Arg


<210> SEQ ID NO 4
<211> LENGTH: 9
<212> TYPE: PRT
<213> ORGANISM: Homo sapiens

<400> SEQUENCE: 4

Asp Val Asp Gly Ala Tyr Met Thr Lys
  1               5


<210> SEQ ID NO 5
<211> LENGTH: 113
<212> TYPE: PRT
<213> ORGANISM: Homo sapiens

<400> SEQUENCE: 5

Ser Leu Asn Asn Gln Phe Ala Ser Phe Ile Asp Lys Val Arg Phe Leu
  1               5                  10                  15

Glu Gln Gln Asn Gln Val Leu Gln Thr Lys Trp Glu Leu Leu Gln Gln
             20                  25                  30

Val Asp Thr Ser Thr Arg Thr His Asn Leu Glu Pro Tyr Phe Glu Ser
         35                  40                  45

Phe Ile Asn Asn Leu Arg Arg Arg Val Asp Gln Leu Lys Ser Asp Gln
     50                  55                  60

Ser Arg Leu Asp Ser Glu Leu Lys Asn Met Gln Asp Met Val Glu Asp
 65                  70                  75                  80

Tyr Arg Asn Lys Tyr Glu Asp Glu Ile Asn Lys Arg Thr Asn Ala Glu
                 85                  90                  95

Asn Glu Phe Val Thr Ile Lys Lys Asp Val Asp Gly Ala Tyr Met Thr
            100                 105                 110

Lys
```

USE OF SOLUBLE CYTOKERATIN-1-FRAGMENTS IN DIAGNOSTICS AND THERAPY

The present application is a nationalization of PCT Application Serial No. PCT/EP02/06473, filed Jun. 12, 2002, which claims priority to German priority application Serial No. 101 30 985.6, filed Jun. 27, 2001.

The present invention relates to the use of novel soluble cytokeratin 1 fragments in medical diagnosis and therapy. It is based on the detection for the first time of the physiological occurrence of certain peptides in the form of soluble cytokeratin 1 fragments in association with a pathological process, in particular in a sepsis or systemic inflammation produced experimentally in a primate. The term "peptides" is used in the present application in the context of a generic term which is intended to include the condensates of amino acids independently of the length of the chain formed, i.e. in particular products which, taking into account their chain length, can be referred to as oligopeptides, polypeptides or proteins.

The present invention has its origin in intensive research work by the Applicant in relation to further improvements of the diagnosis and therapy of inflammations and infections, in particular of inflammations of infectious aetiology and sepsis.

Inflammations are defined very generally as certain physiological reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of numerous serious chronic and acute diseases of individual tissues, organs, organ parts and tissue parts.

Local inflammations are generally part of the healthy immune reaction of the body to harmful effects and hence part of the life-preserving defence mechanism of the body. If, however, inflammations are part of a misdirected reaction of the body to certain endogenous processes, such as, for example, in autoimmune diseases, and/or are of a chronic nature, or if they achieve a systemic extent, as in the case of systemic inflammatory response syndrome (SIRS) or in the case of a severe sepsis caused by infection, the physiological processes typical of inflammatory reactions go out of control and become the actual, frequently life-threatening pathological process.

It is now known that the origin and the course of inflammatory processes are controlled by a considerable number of substances which are predominantly of a protein or peptide nature or are accompanied by the occurrence of certain biomolecules for a more or less limited time. The endogenous substances involved in inflammatory reactions include in particular those which may be counted among the cytokines, mediators, vasoactive substances and acute phase protein and/or hormonal regulators. The inflammatory reaction is a complex physiological reaction in which both the endogenous substances activating the inflammatory process (e.g. TNF-$\alpha$) and deactivating substances (e.g. interleukin-10) are involved.

In systemic inflammations, as in the case of a sepsis or of septic shock, the inflammation-specific reaction cascades are spread in an uncontrolled manner over the whole body and become life-threatening in the context of an excessive immune response. Regarding the current knowledge about the occurrence and possible role of individual groups of endogenous inflammation-specific substances, reference is made, for example, to A. Beishuizen et al., "Endogenous Mediators in Sepsis and Septic Shock", Advances in Clinical Chemistry, Vol. 33, 1999, 55–131; and C. Gabay et al., "Acute Phase Proteins and Other Systemic Responses to Inflammation", The New England Journal of Medicine, Vol. 340, No. 6, 1999, 448–454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, New York, 2001, 756–760, where a modern definition of sepsis is given. In the context of the present application, the terms sepsis and inflammatory diseases used are based on the definitions given in the stated three references.

Whereas at least in Europe the systemic bacterial infection detectable by a positive blood culture long characterized the term sepsis, sepsis is now primarily understood as being systemic inflammation which is caused by infection but, as a pathological process, has great similarities to systemic inflammations which are triggered by other causes. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be involved in an inflammatory process, the ones which are suitable for diagnostic purposes are in particular those whose occurrence is very specific for inflammatory diseases or certain phases of inflammatory diseases, whose concentrations change in a dramatic and diagnostically significant manner and which moreover have the stabilities required for routine determination and reach high concentration values. For diagnostic purposes, the reliable correlation of pathological process (inflammation, sepsis) with the respective biomarker is of primary importance, without there being any need to know its role in the complex cascade of the endogenous substances involved in the inflammatory process.

Such an endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis so that the determination of procalcitonin is also suitable for early diagnosis of a sepsis and for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515–518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329–334; and M. Oczenski et al., "Procalcitonin: a new parameter for diagnosis of bacterial infection in the peri-operative period", European Journal of Anaesthesiology 1998, 15, 202–209; and furthermore H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", in: Sepsis 1998; 2:243–253; and the further literature references cited therein, as typical of recent published reviews.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential new sepsis biomarkers is however, complicated by the fact that frequently very little or nothing is known about the exact function or about the exact reasons for the occurrence of certain endogenous substances which are involved in inflammatory or septic processes.

The results of the experimental testing of a fruitful purely hypothetical approach to the determination of further potential sepsis markers are to be found in DE 198 47 690 A12 and WO 00/22439. There, it is shown that, in the case of sepsis, not only is the concentration of the prohormone procalcitonin increased but also significantly increased concentrations can be observed for other substances which may be included among the peptide prohormones. While the phenomenon described is well documented, the causes of the increase in the concentrations of prohormones in sepsis are still substantially unexplained.

In the present application, results of another, purely experimental approach in the search for further inflammation- or sepsis-specific biomolecules are now reported. These experimental investigations, too, originate in the determination of procalcitonin in relation to systemic inflammatory reactions of infectious aetiology. Thus, it had been observed at a very early stage that the procalcitonin is evidently not formed in the same manner in sepsis as when it is a precursor for the hormone calcitonin. Thus, high procalcitonin levels were also observed in patients whose thyroid had been removed. The thyroid therefore cannot be the organ in which the procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", Sepsis 1998; 2:243–253, the results of experimental investigations which are said to be intended for explaining the formation of procalcitonin in sepsis are reported. In said work, an artificial sepsis is produced by endotoxin administration to primates (baboons), and the experimentally produced states in which the highest procalcitonin concentrations in the blood are reached are determined. A further development of the experimental animal model described in said work serves, in the context of the present application, for determining novel endogenous sepsis-specific biomarkers of a peptic or protein nature, the occurrence of which is characteristic for sepsis or certain forms of sepsis and which therefore permit specific diagnosis of sepsis. The primate model was chosen because of the very great similarity of the physiology of primates and humans and the high cross-reactivity with many therapeutic and diagnostic human reagents.

Since the endogenous substances formed during inflammations are part of the complex reaction cascade of the body, not only are such substances also of diagnostic interest but attempts are currently also being made, with considerable effort, to intervene therapeutically in the inflammatory process by influencing the formation and/or the concentration of individual substances of this type, in order to stop as early as possible the systemic spread of the inflammation, which spread is observed, for example, during sepsis. In this context, endogenous substances which have been shown to be involved in the inflammatory process are also to be regarded as potential therapeutic targets. Attempts based on certain mediators of the inflammatory process and intended to have a positive therapeutic influence on said process are described, for example, in E. A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170; or K. Garber, "Protein C may be sepsis solution", Nature Biotechnology, Vol. 18, 2000, 917–918. These therapeutic approaches are intended to lower the concentrations of inflammation-promoting substances or to inhibit the formation of said substances, and to do so in particular with the use of specific antibodies (against TNF-α or MIF; cf. E. A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170) or to increase the concentration of endogenous substances which have an inhibitory effect in the inflammation cascade (Protein C; K. Garber, "Protein C may be sepsis solution", Nature Biotechnology, Vol. 18, 2000, 917–918). The last-mentioned publication gives an overview of such attempts to have a therapeutic influence on the inflammatory process by influencing the selected endogenous target molecules, which attempts have unfortunately generally met with little success to date. In view of the rather disappointing therapeutic approaches to date, there is great interest in identifying further endogenous biomolecules which are as inflammation- or sepsis-specific as possible and which, as therapeutic targets, also open up new prospects for success in fighting inflammation.

The present invention provides novel soluble peptide fragments which are formed in primates and humans during inflammations caused by infection and are suitable both for inflammation diagnosis and/or sepsis diagnosis and as novel therapeutic targets.

The present invention discloses soluble cytokeratin 1 fragments which, on the basis of their specific occurrence after artificial sepsis triggering by endotoxin administration to primates, have proved to be sepsis-specific or inflammation-specific human peptides.

As will be explained in more detail below in the experimental section, the invention is based on the fact that, after experimental triggering of an artificial sepsis in baboons by endotoxin administration (LPS from *Salmonella Typhimurium*) and working up of liver tissue of the treated animals by gel electrophoresis, a peptide or protein product identifiable only in the treated animals was found. This specific product was isolated from the electrophoresis gel and investigated by mass spectrometry in a manner known per se.

A first partial sequence of the isolated, trypsin-digested protein spot of 12 amino acids with a mass m/z of 692.39 (SEQ ID NO:1) and a second partial sequence of 11 amino acids with a mass m/z of 633.4 (SEQ ID NO:2) could be unambiguously identified, and the sequences could be identified as fragments of the known but essentially completely insoluble cytoskeleton protein cytokeratin 1 (SEQ ID NO:3;

cf. L. Johnson et al., Structure of a gene for the human epidermal 67-kDa keratin; Proc. Natl. Acad. Sci. U.S.A.; 82:1896–1900, (1985); database NiceProt View of SWISS-PROT: Accession number P04264) by comparison of the sequences of these partial peptides with the data of a human database with known protein sequences. The two fragments according to SEQ ID NO:1 and SEQ ID NO:2 correspond to the sequence of the amino acids 185–196 and 277–287, respectively, of the complete cytokeratin 1. A further fragment of the mass spectrum with a mass m/z (z=1) of 999.49 corresponds to a fragment of 9 amino acids. (SEQ ID NO:4; calculated mass 999.45), which corresponds to the partial sequence of the amino acids 289–297 of the complete cytokeratin 1 (SEQ ID NO:3).

From these results it can be safely concluded that the peptide isolated from the electrophoresis gel in the form of a cytokeratin 1 fragment comprises a sequence of amino acids 185–297 (SEQ ID NO:5) of cytokeratin 1. However, the fragment corresponding to this sequence (SEQ ID NO:5) has only a molecular weight of 13615, while the molecular weight determined by gel electrophoresis for the fragment found was 15700±500 Dalton. Fragments which are to be regarded as soluble cytokeratin 1 fragments according to the invention are therefore in particular those in which the fragment 185–297 (SEQ ID NO:5) has been lengthened at one or both of its ends by up to 20 amino acids altogether.

The identification of a certain soluble cytokeratin 1 fragment formed during sepsis in the liver is of considerable scientific, diagnostic and therapeutic interest.

Cytokeratin 1 is a protein from the group consisting of the structural proteins (scleroproteins) which are referred to as cytokeratins or “soft” keratins and, as components of the cytoskeleton, form the so-called intermediate filaments (IF). They impart stability of shape to the cell and are distinguished by high mechanical and chemical stability. Under customary physiological conditions, they, like all keratins, are stable to proteases, and there are only a few organisms, such as, for example, the clothes moth and the fungus *Tritirachium album*, which have enzyme systems which are capable of degrading keratins and using them as a source of nutrition.

Cytokeratins have a structure comprising an α-helical central section of about 310–315 amino acids and end sections adjacent thereto. The cytokeratins can be assigned to two types on the basis of the amino acid sequences occurring in them and their charge. The cytokeratins 9–20 belong to type 1, which includes acidic proteins, while the cytokeratins 1–8 are assigned to type II, which includes basic or neutral proteins. Cytokeratins of type I and of type II occur with formation of heterodimers in certain pairings which are characteristic of certain types of epithelial cells and hence also tissue. In this context, for example, reference may be made to the review article by R. B. Presland et al., in: Crit Rev Oral Biol Med, 11(4):383–408 (2000) or M. Bishr Omary et al., Keratin Modifications and Solubility Properties in Epithelial Cells and in vitro; in: Subcellular Biochemistry, Vol. 31: Intermediate Filaments, N.Y. 1998, pages 105–150.

A determination of IF proteins, which include cytokeratins, has been carried out to date predominantly in association with tumour diagnosis, since the identification of certain IF proteins in metastases or tissue lesions makes it possible to assign them to a tissue of origin or primary tumour.

According to EP-A-0 163 304, such a determination is carried out using suitable specific antibodies by a histodiagnostic method.

For simplifying the procedure for determinations of said type, EP-B1-0 267 355 proposes subjecting the insoluble IF proteins to a treatment which leads to their degradation, and then determining the soluble fragments produced artificially in this manner. It is furthermore stated that cell lesions may also be accompanied by a proteolytic degradation of insoluble structural proteins, so that, under certain conditions, α-helical fragments may also be found in body fluids.

EP-B1-0 267 356 is related but is not concerned with the direct determination of soluble fragments of IF proteins but of antibodies formed against such fragments in serum.

EP-B1-0 337 057 further develops the method from EP-B1-0 267 355 as a method for identifying the origin of a cell sample or tissue sample, a certain standard for use in the determinations being proposed.

The determination of soluble cytokeratin 19 fragments for differential diagnosis, prognosis, therapy efficiency monitoring and follow-up observation in the care of bronchial carcinomas is also described in P. Stieber, CYFRA 21-1 (Cytokeratin 19 fragments) in: L. Thomas, Labor und Diagnose, pages 987–992. The versatility of the cytokeratins, once again in particular the cytokeratins 8, 18 and 19, as tumour markers is also discussed in Torgny Stigbrand, The Versatility of Cytokeratins as Tumor Markers, Tumor Biol 2001, 22:1–3.

All of the above cases are concerned primarily with the determination of fragments of the cytokeratins 8, 18 and 19. Among all soluble cytokeratin fragments discussed in the literature, there are no soluble cytokeratin 1 fragments, and there is also a lack of any information about a possible occurrence of such cytokeratin 1 fragments in certain pathological conditions.

It has long been believed that cytokeratin 1—together with cytokeratin 10—is found substantially only in a single, immunologically isolated cell type, namely in suprabasal well differentiated keratinocytes.

An unusual occurrence of cytokeratin 1 and an unexpected involvement in a pathogenic process are described in the papers by Steven D. Lucas et al., Identification of a 35 kD Tumor-Associated Autoantigen in Papillary Thyroid Carcinoma, Anticancer Research 16:2493–2496 (1996), and Steven D. Lucas et al., Aberrantly Expressed Cytokeratin 1, A Tumor-Associated Autoantigen in Papillary Thyroid Carcinoma, Int. J. Cancer 73, 171–177 (1997) in relation to papillary thyroid carcinoma (PTC). Cytokeratin 1 can be detected in the form of a 35 kD fragment in a solubilisate of PTC cells by immunoprecipitation with the aid of patient sera. (Auto)antibodies against cytokeratin 1 are found in the patient sera. There is no mention of soluble cytokeratin 1 fragments from body fluids and/or body tissues.

The detection, according to the invention, of a soluble cytokeratin 1 fragment in the liver of primates in which an artificial sepsis was triggered by toxin administration, with simultaneous complete absence of such a fragment in otherwise completely identically treated samples of control animals, is extremely surprising in view of all knowledge to date about the occurrence, the properties and the role of cytokeratin 1. Since the occurrence has been observed only in the treated animals, in particular a very short time after sepsis triggering by toxin administration, it is possible to utilize this fact for providing a promising method for diagnosing sepsis, infections and inflammation by determination of this fragment formed by the organism.

Since it may be assumed that, due to an increased sepsis- or inflammation-specific protease activity (and/or reduced inhibition of such a protease activity by the protease inhibitors usually involved in the regulation), the detected fragment is formed by a proteolytic route from the complete cytokeratin 1, but not by a modified expression of a corresponding gene, it is to be expected that further soluble cytokeratin 1 fragments which correspond to the "remaining" regions of the proteolytically degraded complete cytokeratin 1, in particular its α-helical region, can also be found and, similarly to the above-mentioned fragments, are suitable for determination. The determination of such further fragments is also to be included expressly as a variant of the present invention.

Since cytokeratin 1 is found in the respective cells as a rule together with cytokeratin 10, it also appears possible that cytokeratin 10 fragments too will be formed in the case of the infection- or inflammation-related increased proteolytic activity of the organism with lesions of cells which contain the two cytokeratins 1 and 10, and, like cytokeratin 1 fragments, can be determined. The cytokeratin 1 fragments may also be present as soluble adducts or aggregates, for example in the form of aggregates with cytokeratin 10 fragments.

It is furthermore within the scope of the present invention to determine cytokeratin 1 fragments which, in the range of the sequences SEQ ID NO:1, SEQ ID NO:2 and SEQ ID NO:5, exhibit certain deviations from the specific amino acid partial sequences described, in particular when individual, patient-specific deviations or polymorphisms can be observed in the range of said sequences. The agreement with said specific sequences is, however, likely to be higher than 75%, and in particular also higher than 90% or 95%.

The determination can be effected by any desired suitable detection method, but the determination in a body fluid of a patient by an immunodiagnostic method using suitable selective antibodies appears most advantageous from practical points of view.

The fact that a certain soluble fragment of the essentially completely insoluble cytokeratin 1 was detectable for the first time on experimentally triggering sepsis thus provides the possibility of utilizing such cytokeratin 1 fragments for diagnostic and/or therapeutic purposes. To this end, cytokeratin 1 fragments can, if required, also be specifically prepared by methods which are now part of the prior art, by synthesis, genetic engineering or hydrolysis, in particular proteolysis.

Furthermore, cytokeratin 1 fragments or suitable partial sequences thereof can be used by known processes of the prior art also for producing specific polyclonal and in particular monoclonal antibodies which are suitable as aids for the diagnostic determination of cytokeratin 1 fragments in body fluids of a patient and/or also as potential therapeutic agents. The production of suitable monoclonal antibodies against known peptide partial sequences is now part of the general prior art and need not be described in particular. Furthermore, antibody production using techniques of direct genetic immunization with a corresponding DNA should also be mentioned expressly. It is therefore within the scope of the present invention to use, for example, a cDNA of cytokeratin 1 fragments for immunization, since it has been found in the past that the spectrum of obtainable antibodies can be extended with the use of such immunization techniques. However, it is also possible to use known and commercially available antibodies against cytokeratins.

In the immunological determination of soluble cytokeratin 1 fragments, it is possible in principle to proceed as described, for example, for the selective procalcitonin determination in P. P. Ghillani et al., "Monoclonal antipeptide antibodies as tools to dissect closely related gene products", the Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851; reference being made expressly and additionally also to the immunization techniques described there, which represent a possibility for obtaining monoclonal antibodies also against partial sequences of cytokeratin 1 fragments. A person skilled in the art can consult relevant standard works and publications for variations of the techniques described and/or further immunization techniques and can apply them in context.

Cytokeratin 1 fragments having the partial sequences according to SEQ ID NO:1, SEQ ID NO:2, SEQ ID NO:4 and/or SEQ ID NO:5 or partial peptides thereof, or cytokeratin 1 fragments which are formed in the proteolytic cleavage of the α-helical part of cytokeratin 1 in addition to the above detected and characterized fragment, can serve, on the basis of the available results, as specific marker peptides (biomarkers) for diagnosis, for prognosis and for monitoring of the course of inflammations and infections (in particular of systemic infections of the sepsis type). As in the case of the determination of procalcitonin, the determination of at least the specific soluble cytokeratin 1 fragment found can be carried out for the differential early diagnosis or for the diagnosis and for the prognosis, for the assessment of the severity and for the therapy-accompanying assessment of the course of sepsis and infections, in such a method the content of a certain cytokeratin 1 fragment being determined in a sample of a biological fluid or of a tissue of a patient and the presence of an inflammation, of a severe infection or of a sepsis being concluded from the established presence and/or amount of the certain peptide and the result obtained being correlated with the severity of the sepsis, and the possible treatments and/or the prospects of the treatment being estimated.

Cytokeratin 1 fragments (or any DNA segments coding for said fragments) can, however, also be used in preventive medicine or therapy.

The fact that it has recently been found that cytokeratin 1 plays an important role as a type of surface receptor for the so-called high molecular weight kinin (HK), whose binding is an important step in the triggering of the bradykinin cascade, plays an important role for therapeutic realization of the novel discoveries according to the invention. In this context, reference is made to the results to be found in the following papers: (a) Zia Shariat-Madar et al., Kininogen-Cytokeratin 1 Interactions in Endothelial Cell Biology, TCM Vol. 9, No. 8, 1999, 238–244; (b) Zia Shariat-Madar et al., Mapping Binding Domains of Kininogens on Endothelial Cell Cytokeratin 1; J. Biol. Chem. 273, No. 11, 7137–7145, 1999; (c) K. Joseph et al., Factor XII-dependent Contact Activation on Endothelial Cells and Binding Proteins gC1qR and Cytokeratin 1, Thromb. Haemost. 85:119–124, 2001; (d) K. Joseph et al., Activation of the Kinin-Forming Cascade on the Surface of Endothelial Cells, Biol. Chem. Vol. 382:71–75 (2001); (e) A. Kaplan et al., Activation of the Plasma Kinin Forming Cascade along Cell Surfaces, Int Arch Allergy Immunol 2001; 124:339–342.

In the abovementioned publication (b), a sequence range which is in the immediate edge region of the experimentally detected cytokeratin 1 fragment with sequence SEQ ID NO:5 was determined as the binding site for said HK to cytokeratin 1.

The kinins of the so-called bradykinin cascade have, inter alia, vasodilatory, hypotensive and vascular permeability-increasing effects. Since such symptoms are observed in a sepsis and are among the physiological processes critical for the patient, it cannot be ruled out that there is a causal relationship between said clinical symptoms and a sudden occurrence of soluble cytokeratin 1 fragments in the blood, triggered by the sepsis and associated with a direct effect on the bradykinin cascade. Both an enhancing effect in the sense of an increased, no longer localized supply of activating HK receptors and an effect in the sense of a counteraction, for example by binding and deactivation of kinins secreted in excess are conceivable, and it is also conceivable that such effects are sequential in a concentration-dependent manner.

This makes cytokeratin 1 fragments also potential promising therapeutic targets for the therapy of sepsis and similar severe inflammations. In this context, depending on which of the abovementioned effects proves to be the more important, either soluble cytokeratin 1 fragments in the form of drugs can be administered to a patient suffering from sepsis or at risk from sepsis, or the concentration of such fragments can be reduced by administering binding antibodies or by extracorporeal removal of such fragments through a lavage of the blood or plasmapheresis by means of affinity absorption. The kinin cascade can be influenced thereby, which can prove to be life-saving.

If soluble cytokeratin 1 fragments as such are used for therapeutic purposes in drugs, they can also be synthesized by targeted proteolysis using suitable endoproteases, in particular with the use of cytokeratin 1 isolates or concentrates which can be prepared from readily available materials utilizing the known solubility properties of the different cytokeratins in buffers. If endogenous material of a patient (autologous or autogenous material) is used as starting material, optimum tolerance and efficacy are ensured.

Those molecules which contain the chosen cytokeratin 1 fragment in posttranslational modified form, e.g. in glycoslyated or phosphorylated form, or in a form substituted by pharmaceutical excipients, e.g. polyethylene glycol radicals, should also be regarded as therapeutically usable cytokeratin 1 fragments.

Figure 2:
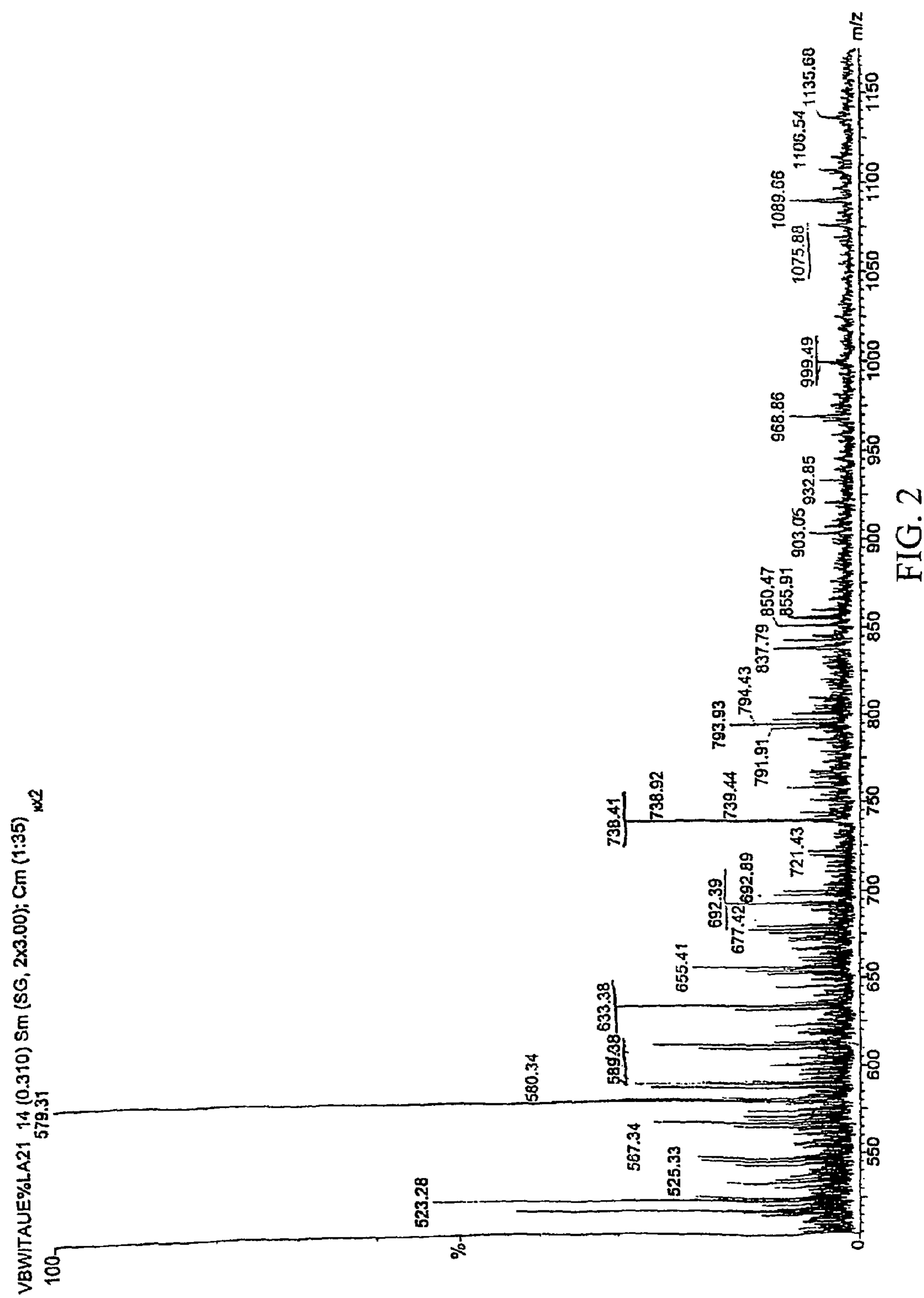
Figure 3A:
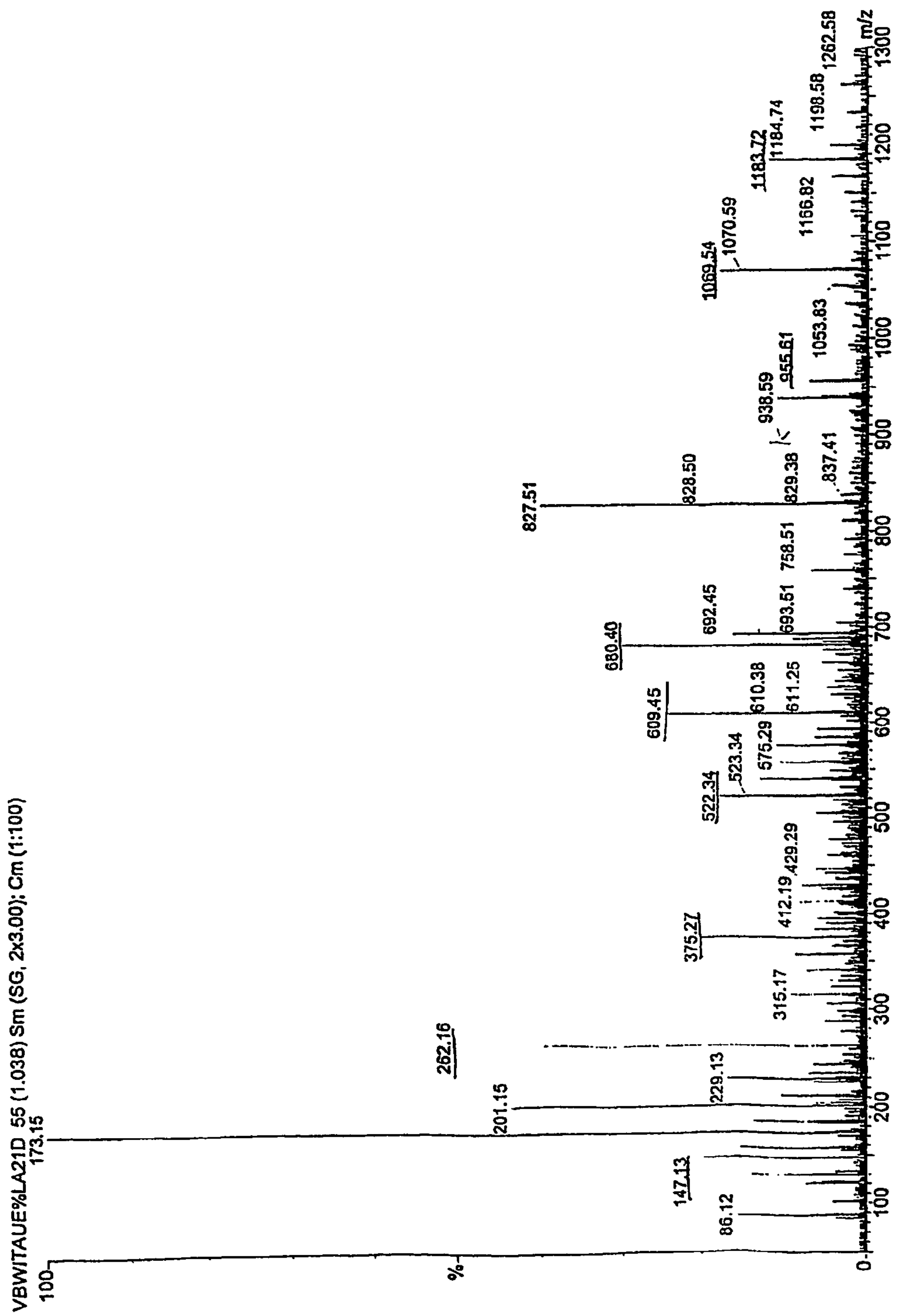
Figure 3B:
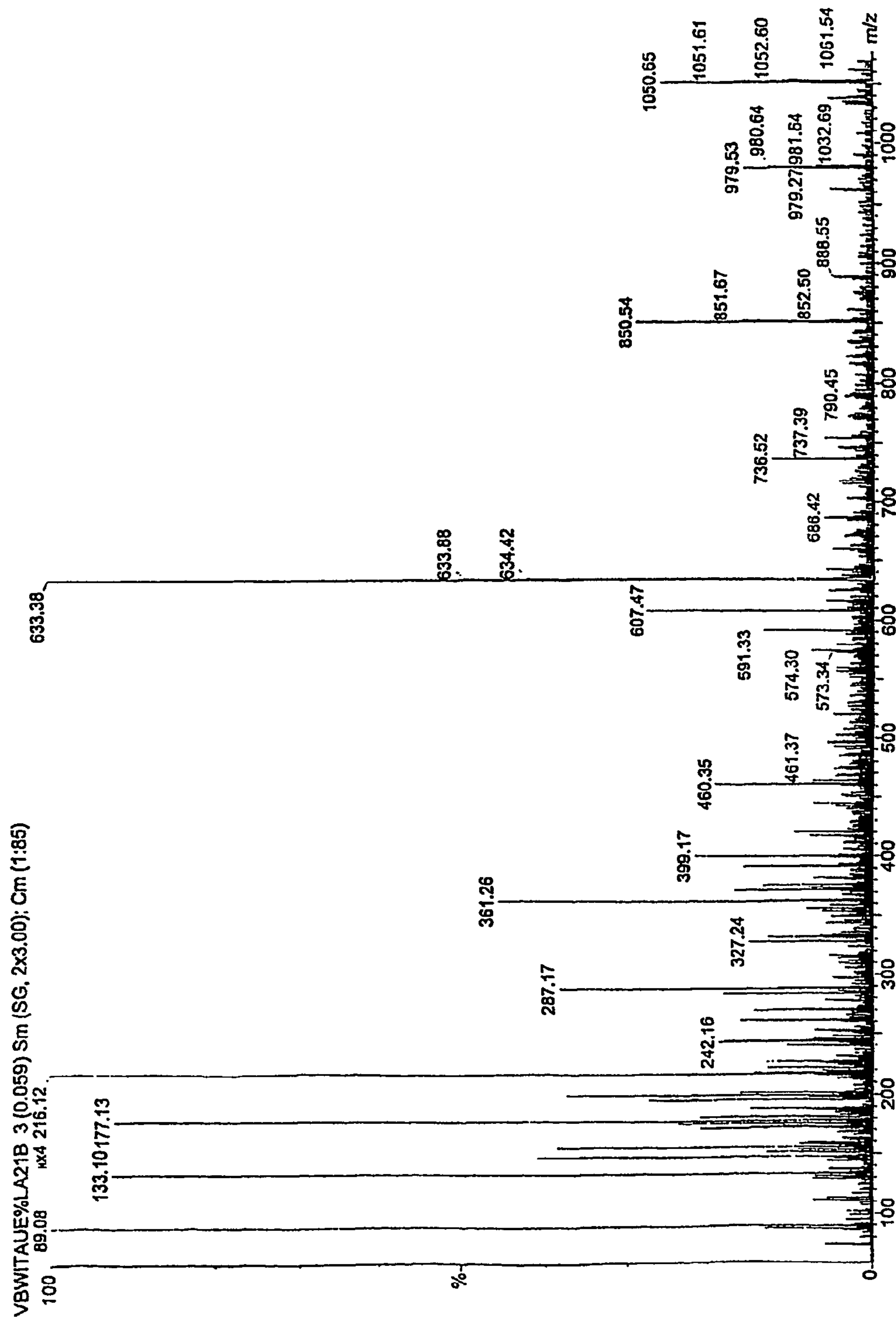
Figure 4:
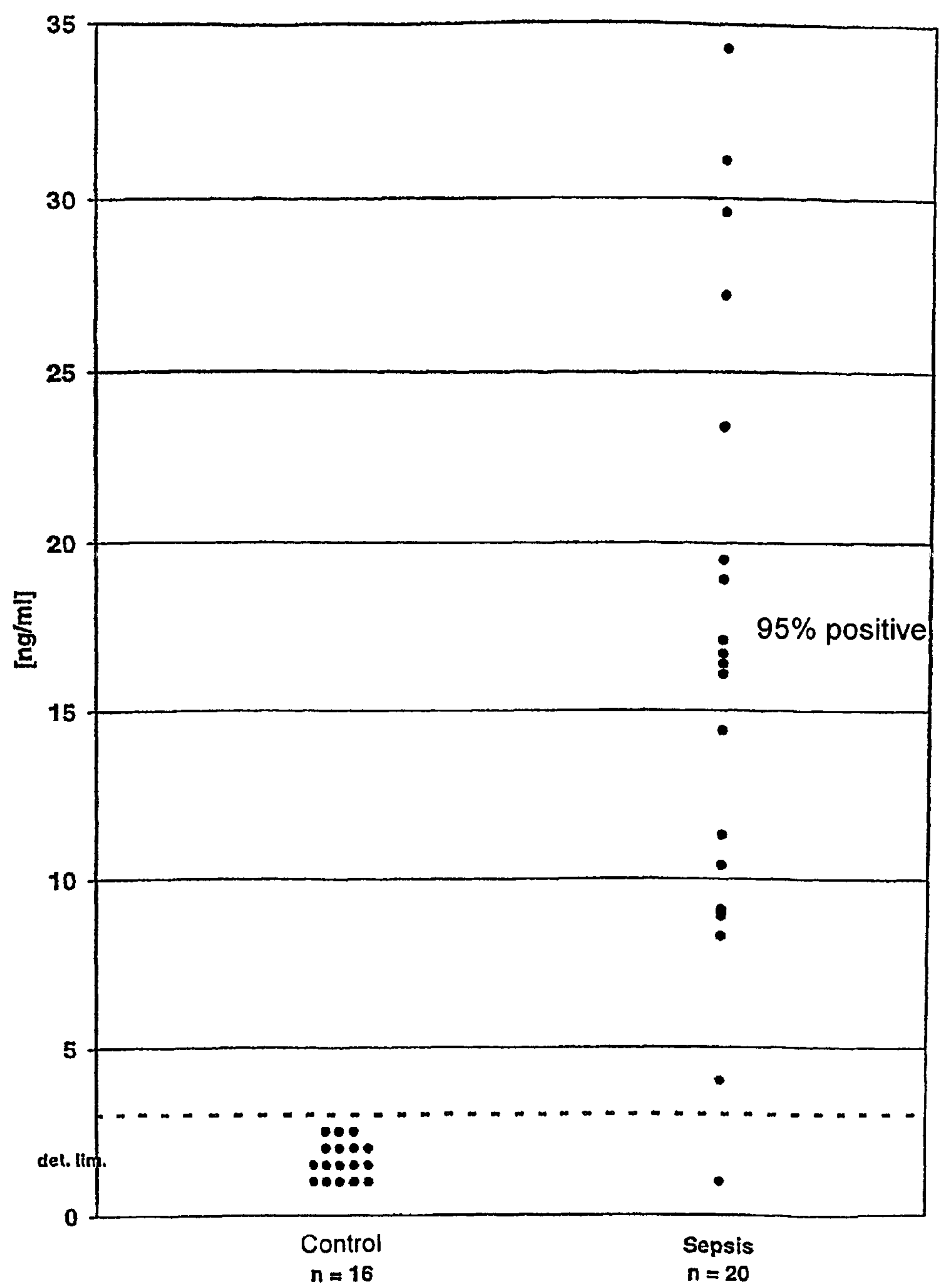

The discovery and the identification of a specific cytokeratin 1 fragment are described in more detail below, reference being made to the attached sequence listing. The figures show the following:

FIG. 1 shows views of 2D electrophoresis gels which permit a comparison of the spot patterns of cytoplasmic liver cell protein of a healthy baboon (A) with the liver cell proteins of a baboon 5 h after a sepsis induced by LPS administration (B). The arrow indicates the position of the sepsis-specific product according to the invention (cytokeratin 1 fragment) which is distinguished in diagram (B) by a circle;

FIG. 2 shows the mass spectrum of the trypsin-digested isolated product identified by 2D gel electrophoresis, and FIG. 3*a* shows the results of a tandem electrophoresis of a selected peptide fragment of the trypsin digestion with a charge/mass ratio of 692.39; and FIG. 3*b* shows the results of a tandem electrophoresis of a further selected peptide fragment of the trypsin digestion with a charge/mass ratio of 633.38;

FIG. 4 shows the results of the determination of the soluble cytokeratin 1 fragment in the sera of 20 sepsis patients in comparison with a group of 16 control persons (blood donors).

1. Infection Simulation by Endotoxin Administration in an Animal Model (Baboons).

On the basis of the experiments carried out with baboons for the stimulation of procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659–3663; H. Redl et al., "Non-Human Primate Models of Sepsis", in: Sepsis 1998; 2:243–253), baboons (male, about 2 years old, weighing from 27 to 29 kg) were each intravenously administered 100 μg of LPS (lipopolysaccharide from *Salmonella Typhimurium*, source: Sigma) per kg body weight. From 5 to 5.5 h after the injection, the animals were sacrificed by intravenous administration of 10 ml of doletal. Within 60 min of their death, all organs/tissues were dissected and were stabilized by freezing in liquid nitrogen.

During the further processing, 1.5 ml of buffer A (50 mM Tris/HCl, pH 7.1, 100 mM KCl, 20% of glycerol) were added to samples of the individual frozen tissues (1 g) while cooling with nitrogen, and the samples were pulverized in a porcelain mortar to give a powder (cf. J. Klose, "Fractionated Extraction of Total Tissue Proteins from Mouse and Human for 2-D Electrophoresis", in: Methods in Molecular Biology, Vol. 112: 2-D Proteome Analysis Protocols, Humana Press Inc., Totowa, N.J.). After subsequent centrifuging for 1 hour at 100,000 g and +4° C., the supernatant obtained was recovered and was stored at −80° C. until required for further processing.

Using the tissue extracts obtained in this manner, an investigation was first carried out to determine in which of the tissues investigated the largest amounts of the known sepsis biomarker procalcitonin can be produced by endotoxin administration. In the determined tissue having the highest level of procalcitonin formation, further previously unidentified protein products which occurred only after endotoxin administration were then sought by means of differential proteome analysis. For this purpose, tissue samples of untreated baboons were used as control tissue samples, the sacrificing and obtaining of samples having been effected under conditions identical to those in the case of the treated animals.

2. Determination of Baboon Tissues Having the Highest Level of Procalcitonin Formation After Endotoxin Injection Samples of the individual tissues were investigated with the aid of an immunoluminometric test which operates (similarly to the LU-MItest® PCT of the Applicant, developed for the determination of human procalcitonin) with, on the one hand, an antibody against baboon calcitonin, immobilized on polystyrene tubes, and a monoclonal antibody marked with an acridinium ester and directed against the N-terminus of baboon procalcitonin. With the aid of this test, the contents of baboon procalcitonin in the individual samples were determined after calibration of the test using recombinant human procalcitonin.

The experiments showed that liver tissue gives the largest amount of procalcitonin. The protein extracts from baboon liver which were obtained in the manner described at the outset were therefore used for searching for novel sepsis-specific biomarkers.

3. Proteome Analysis Using Cytoplasmic Liver Cell Proteins of Baboons.

Cytoplasmic liver cell protein extracts of, on the one hand, healthy baboons (control) and, on the other hand, baboons which had been injected with LPS were used in a proteome analysis. In the initial analytical 2D gel electrophoresis, liver extract containing 100 μg of protein was stabilized to 9M urea, 70 mM DTT, 2% ampholyte pH 2–4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034–1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28–32).

For evaluation, the protein spot patterns of the samples of untreated animals were compared with the protein spot patterns which resulted from liver tissue samples of treated animals. Substances which occurred in no control sample but additionally in all treated animals were selected for further analytical investigations. FIG. 1 shows a comparison of the 2D electrophoresis gels for a control sample (A) and a sample of a treated animal (B), the additional protein spot in (B) corresponding to the novel soluble cytokeratin 1 fragment, the position of which is singled out by an arrow and a circle.

The novel specific proteins identified in the protein spot pattern of the analytical 2D gel electrophoresis were then prepared by means of preparative 2D gel electrophoresis using 350 μg of protein (once again cf. (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255–262).

The protein spots preselected for the further analysis were cut out of the gel, using the method which is described in A. Otto et al., "Identification of human myocardial proteins separated by two-dimensional electrophoresis using an effective sample preparation for mass spectrometry", Electrophoresis 1996, 17, 1643–1650, trypsin-digested and then analyzed by mass spectroscopy, in particular with the use of mass spectrometric investigations as described and discussed, for example, in G. Neubauer et al., "Mass spectrometry and EST-database searching allows characterization of the multi-protein spliceosome complex", in: nature genetics vol. 20, 1998, 46–50; J. Lingner et al., "Reverse Transcriptase Motifs in the Catalytic Subunit of Telomerase", in: Science, Vol. 276, 1997, 561–567; M. Mann et al., "Use of mass spectrometry-derived data to annotate nucleotide and protein sequence databases", in: TRENDS in Biochemical Sciences, Vol. 26, 1, 2001, 54–61. After an ESI (ElectroSprayIonization), the trypsin-digested samples were subjected to tandem mass spectrometry. A Q-TOF mass spectrometer having a so-called nanoflow-Z-Spray ion source from Micromass, UK, was used. The procedure corresponded to the working instructions of the equipment manufacturer.

4. Identification of a Soluble Cytokeratin 1 Fragment

As shown in FIGS. 1(A) and 1(B), liver cell extracts of baboons to which an LPS injection had been administered contained, inter alia, a novel protein for which a molecular weight of about 15,700±500 Dalton was estimated on the basis of the gel electrophoresis data in comparison with marker substances having a known molecular weight, while an isoelectric point of from about 5.5 to 6.5 was estimated from the relative position of the protein from the first dimension.

This protein was analyzed as above by mass spectrometry, and it was possible to assign to the two trypsin fragments according to FIGS. 3*a* and 3*b* the amino acid sequences SEQ ID NO:1 and SEQ ID NO:2, which proved to be partial sequences of the known sequence of cytokeratin 1 (SEQ ID NO:3; cf. L. Johnson et al., Structure of a gene for the human epidermal 67-kDa keratin; Proc. Natl. Acad. Sci. U.S.A.; 82:1896–1900, (1985); database NiceProt View of SWISS-PROT: Accession number P04264). The two fragments according to SEQ ID NO:1 and SEQ ID NO:2 correspond to the sequence of the amino acids 185–196 and 277–287, respectively, of the complete cytokeratin 1. A further fragment of the mass spectrum having a mass m/z (z=1) of 999.49 corresponds to a fragment of 9 amino acids (SEQ ID NO:4; calculated mass 999.45) which corresponds to the partial sequence of the amino acids 289–297 of the complete cytokeratin 1 (SEQ ID NO:3).

These results permit the safe conclusion that the peptide in the form of a cytokeratin 1 fragment, isolated from the electrophoresis gel, comprises the sequence of the amino acids 185–297 (SEQ ID NO:5) of cytokeratin 1. However, the fragment corresponding to this sequence (SEQ ID NO:5) has only a molecular weight of 13,615, while the molecular weight of the fragment found, determined by gel electrophoresis, was 15,700±500 Dalton. Consequently, in particular those fragments in which the fragment 185–297 (SEQ ID NO:5) has been lengthened at one or both of its ends by up to 20 amino acids altogether are to be regarded as soluble cytokeratin 1 fragments according to the invention.

5. Determination of the Soluble Cytokeratin 1 Fragment in Sera

The serum concentrations of the above-mentioned soluble cytokeratin 1 fragments were determined in 20 sera of sepsis patients in whom high values for the sepsis marker procalcitonin (PCT) had been found. In 95% of the sepsis sera, greatly increased concentrations (more than 3 ng/ml) were found.

For the exploratory determinations in sepsis sera, a competitive luminescence immunoassay specially developed for this purpose was used, in which immunoassay sheep antibodies against a peptide which comprised a partial sequence of the cytokeratin 1 fragment, which included the amino acids 214 to 229 of SEQ ID NO:3, were used. The synthetic peptide used for obtaining antibodies and as competitor is commercially available under the name peptide PLY17 (Jerini BioTools GmbH).

The following procedure was used for carrying out the determination:

Polystyrene tubes (from Greiner) were coated with 100 ng of peptide (PLY17; SEQ ID NO:1) in 300 μl of PBS. After incubation for 20 hours at room temperature, washing was effected with 2×4 ml of PBS, containing 1% of BSA. The peptide-coated tubes were then used as a solid phase for carrying out the subsequent measurements in which the immobilized peptides and the cytokeratin 1 fragments from the sample competed for a sheep antibody against the above-mentioned partial peptide sequence, which antibody had been added in the form of an antiserum.

The following procedure was used for the measurement:

1. pipette 100 μg of the sample (sepsis serum or control serum or calibrator solution) into the above-mentioned tubes;
2. pipette 200 μl of antiserum (diluted 1:5000 with PBS);
3. incubate for 3 h at room temperature with shaking;
4. wash the unbound antibody out of the tubes (filled 4× with 1 ml of PBS and decanted);
5. add an acridinium ester-marked donkey anti-sheep antibody (B.R.A.H.M.S Diagnostica) in 300 ml of PBS, 1% of BSA for marking the solid phase-bound antibodies;
6. after incubation for 2 h at room temperature, remove the unbound marking antibody and wash as under 4;

7. measure the acridinium ester bound to the solid phase in a known manner by means of a luminometer (from Berthold).

For the preparation of a calibration curve, solutions containing known amounts of the above-mentioned synthetic peptide were used, and the concentrations of the soluble cytokeratin 1 fragment were determined by comparison of the measured values for the sepsis sera with the calibration curve.

A graph of the measured results is shown in FIG. 4. Even with the provisional, very simple and insensitive competitive measurement procedure described, very good sensitivity of the determination of the cytokeratin 1 fragments in the case of sepsis is evident.

The cytokeratin 1 fragment found is to be designated as a novel protein (or peptide) whose presumably proteolytic formation was observed for the first time after contact of the primate organism with the endotoxins administered. It has to date only been possible to speculate about a possible natural role of the fragment. However, its identification for the first time and the documented high specificity make it a promising diagnostic target and a novel interesting target for therapeutic intervention.

It is furthermore within the scope of the present invention to use the cytokeratin 1 fragment identified or a related fragment, optionally also a part-fragment, as pharmaceutical active substances. The invention accordingly also relates to pharmaceutical compositions which contain, as the actual active substance, one of the peptides according to the invention or antibodies produced against these peptides and prepared for administration to patients together with a suitable pharmaceutical carrier.

The invention claimed is:

1. A method for diagnosis of systemic inflammation and/or systemic infection in an animal or patient, comprising testing a biological sample from said animal or patient for the presence of a soluble cytokeratin 1 fragment or soluble cytokeratin 1 fragments, wherein the soluble cytokeratin 1 fragment consists of the amino acid sequence of amino acids 151–510 of the complete amino acid sequence of cytokeratin 1 (SEQ ID NO: 3) or the soluble cytokeratin 1 fragment has a molecular weight, as determined by gel electrophoresis of, 15,700±500 Dalton, has an amino acid sequence comprising amino acids 185–297 (SEQ ID NO: 5) of the complete amino acid sequence of cytokeratin 1 (SEQ ID NO: 3) and one or more additional amino acids at one or both ends of SEQ ID NO: 5 for a total of up to 20 adjacent amino acids of the complete amino acid sequence of cytokeratin 1 and wherein the presence of said fragment or fragments is indicative of the presence of sepsis, sepsis-like systemic inflammation and/or infection.

2. The method according to claim 1, wherein said biological sample is a biological fluid or a tissue sample.

3. The method according to claim 1, wherein the soluble cytokeratin 1 fragment has a molecular weight, as determined by gel electrophoresis, of 15,700±500 Dalton, has an amino acid sequence of amino acids 185–297 (SEQ ID NO: 5) and one or more additional amino acids at one or both ends of SEQ ID NO: 5 for a total of up to 20 adjacent amino acids wherein said amino acid sequence corresponds to the complete amino acid sequence of cytokeratin 1 or a sequence of at least 90% identity with the complete amino acid sequence of cytokeratin 1 and wherein said fragment is detectable by an antibody specific for an epitope of a peptide consisting of amino acids 214 to 229 of SEQ ID NO: 3.

4. The method according to claim 1, wherein the presence of a soluble cytokeratin fragment or soluble cytokeratin fragments is determined by an immunodiagnostic method of determination.

5. The method according to claim 3, wherein the soluble cytokeratin 1 fragment determined has the amino acid sequence of amino acids 185–297 (SEQ ID NO: 5) of the complete amino acid sequence of cytokeratin 1 (SEQ ID NO: 3) and up to 20 adjacent amino acids of the complete amino acid sequence of cytokeratin 1.

6. The method according to claim 5, wherein the soluble cytokeratin 1 fragment determined has the amino acid sequence of amino acids 185–297 (SEQ ID NO: 5) of the complete amino acid sequence of cytokeratin 1 (SEQ ID NO: 3).

7. The method according to claim 1, wherein said soluble cytokeratin 1 fragment or fragments are present at a concentration of at least 3 ng/ml.

* * * * *

UNITED STATES PATENT AND TRADEMARK OFFICE

CERTIFICATE OF CORRECTION

PATENT NO. : 7,132,246 B2
APPLICATION NO. : 10/480848
DATED : November 7, 2006
INVENTOR(S) : Bergmann et al.

It is certified that error appears in the above-identified patent and that said Letters Patent is hereby corrected as shown below:

Title Page

Please insert the following:

Item -- (73) Assignee: B.R.A.H.M.S Aktiengesellschaft, Hennigsdorf, Germany --

Signed and Sealed this

Nineteenth Day of August, 2008

JON W. DUDAS
*Director of the United States Patent and Trademark Office*